United States Patent [19]

Sheard et al.

[11] Patent Number: 5,330,750

[45] Date of Patent: Jul. 19, 1994

[54] NAIL LACQUERS

[75] Inventors: Christine Sheard; Julia E. Fisher, both of Nottinghamshire, United Kingdom

[73] Assignee: The Boots Company Plc., England

[21] Appl. No.: 30,038

[22] PCT Filed: Sep. 14, 1991

[86] PCT No.: PCT/EP91/01753

§ 371 Date: Mar. 18, 1993

§ 102(e) Date: Mar. 18, 1993

[87] PCT Pub. No.: WO92/05762

PCT Pub. Date: Apr. 16, 1992

[30] Foreign Application Priority Data

Sep. 29, 1990 [GB] United Kingdom ............... 9021252.3

[51] Int. Cl.$^5$ ................................................ A61K 7/04
[52] U.S. Cl. ...................................... 424/61; 424/401; 424/682; 424/693; 514/772.3
[58] Field of Search ................. 424/61, 682, 693, 401; 514/772.3

[56] References Cited

U.S. PATENT DOCUMENTS

| | | | |
|---|---|---|---|
| 4,646,765 | 3/1987 | Cooper et al. | 132/73 |
| 4,873,077 | 10/1989 | Thompson et al. | 424/61 |

FOREIGN PATENT DOCUMENTS

| | | |
|---|---|---|
| 1453089 | 9/1966 | France . |
| 811336 | 8/1982 | South Africa . |
| 1177420 | 1/1970 | United Kingdom . |

OTHER PUBLICATIONS

Data Sheet Jun. 1988 Croxton and Garry.

*Primary Examiner*—Thurman K. Page
*Assistant Examiner*—Jyothsna Venkat
*Attorney, Agent, or Firm*—Ostrolenk, Faber, Gerb & Soffen

[57] ABSTRACT

A nail lacquer composition which comprises 0.05 to 10% by weight of crystalline inorganic fibers having an aspect ratio of at least 2:1 is described. Preferred inorganic fibers are calcium salts such as calcium metasilicate and calcium sulphate. The use of such fibers has been found to give nail lacquer compositions with excellent wear and adhesion properties.

18 Claims, No Drawings

NAIL LACQUERS

The present invention relates to nail lacquer compositions and in particular to nail lacquers containing at least one fibrous additive.

Organic fibres such as nylon and silk have been incorporated into nail varnishes and associated products for a number of years. Nail varnishes containing such fibres are claimed to have improved properties including increased wear and protection against nail splitting, cracking, peeling and breaking. However, nylon and silk fibres have also been associated with certain disadvantages in nail varnish systems because they are soft and flexible and because the adhesion between the fibres and the nail varnish resin is low.

Surprisingly, the applicants have now found that the use of certain inorganic fibres in nail lacquers provides compositions having superior properties.

Accordingly, the present invention provides a nail lacquer composition which comprises 0.05 to 10%, preferably 0.05 to 5%, by weight of crystalline inorganic fibres having an aspect ratio of at least 2:1, preferably of at least 4:1, wherein said fibres are calcium silicate fibres or calcium sulphate fibres.

The term "nail lacquer" as used herein includes nail varnishes, top coats, base coats, nail hardeners and ridge fillers. Nail varnishes commonly contain colour pigments and pearlisers to produce an attractive cosmetic finish. In contrast, top coats are usually clear lacquers which may have a lower resin content and relatively high diluent content compared to nail varnishes. They are intended to give a fast drying, hardened, high gloss finish. Preferred nail varnish and top coat compositions according to the invention comprise 0.05 to 5%, preferably 0.05 to 2.5%, most preferably 0.1 to 1% by weight of inorganic fibres.

Base coats, nail hardeners and ridge fillers may be clear or pigmented nail lacquer compositions. They may contain higher levels of resin than nail varnishes to provide a smooth even base film with good adhesion to the nail surface and they may also contain agents which improve the properties of the nails themselves. Preferred base coats, nail hardeners and ridge fillers according to the invention comprise 0.05 to 10%, preferably 0.1 to 10%, most preferably 0.5 to 5% by weight of inorganic fibres.

The use of fibres in nail lacquers enhances matrix formation, improving the strength and wear of the lacquer film. Fibres may also act as terminators during crack formation thereby reducing the susceptibility of the dried lacquer to chipping. The inorganic fibres of use in the present invention achieve these advantages without significantly affecting the viscosity, rheology or gloss of the nail lacquer compositions.

Surprisingly, the applicants have found that the use of inorganic fibres in nail lacquers is not associated with many of the disadvantages associated with the known use of silk or nylon fibres. The crystalline inorganic fibres produce a hard, rough film which provides keying sites, ensuring good adhesion between the fibres, resin and nail surface, and enhances the wear of the nail lacquer. Furthermore, inorganic fibres do not substantially reduce the flexibility or increase the brittleness of the dried lacquer films.

The crystalline inorganic fibres of use in the present invention are substantially insoluble in typical solvents used in nail lacquer compositions. Suitable fibres are also resistant to attack by the dilute mineral or organic acids used to produce the suspending matrix of nail lacquer compositions. The use of calcium silicate or calcium sulphate fibres is preferred. Calcium metasilicate crystal fibres are found in a natural mineral source, wollastonite, commercially available from Croxton +Garry Ltd, UK under the trade name Kemolit Wollastonite. The aspect ratio of Kemolit Wollastonite is between 10:1 and 20:1. However, the use of single crystal whisker fibres of calcium sulphate is particularly preferred. Calcium sulphate whisker fibres may be derived by hydrothermal synthesis from the natural mineral source gypsum and are commercially available in the anhydrous or hemihydrate form under the trade name Franklin Fiber Filler (Croxton +Garry Ltd, UK). The average aspect ratio of Franklin Fiber Filler is 30:1.

The compositions of the present invention may be prepared by low shear mixing of the inorganic fibres or a suspension thereof into a conventional nail lacquer base formulation. Alternatively, the fibres may be incorporated at an earlier stage of the formulation process without affecting the advantageous properties of the resultant compositions.

The nail lacquer compositions according to the invention contain at least one film former, typically 8 to 30% by weight of nitrocellulose or 12 to 55% by weight of acrylic acid esters such as methyl, ethyl and butylmethacrylates. Preferred nail lacquer compositions contain at least one nitrocellulose film former. The adhesion, gloss and wear of nitrocellulose films are generally improved by the addition of one or more secondary resins, which may comprise 2 to 20% by weight of the nail lacquer composition. Preferred resins are synthetic resins such as aryl sulphonamideformaldehyde, acrylic and polyester resins. One or more plasticisers such as castor oil and dibutyl phthalate may also be incorporated into nitrocellulose lacquers to improve their flexibility, flow properties and gloss. Typical nitrocellulose nail lacquer compositions contain 2 to 12% by weight of suitable plasticiser.

Solvent is required to dissolve the film former and to allow the formation of a homogeneous mixture of ingredients. Solvent may comprise 10 to 60% by weight of the nail lacquer composition. Generally a mixture of high and low boiling point solvents is used to achieve a rapid drying time combined with easy even application. Suitable solvents include acetone, diacetone alcohol, organic esters such as ethyl acetate and butyl acetate and acrylic solvents such as toluene and isopropyl alcohol. Diluents miscible with nitrocellulose or acrylic solvents are often incorporated to reduce the total amount of solvent required and to stabilise the viscosity of the lacquer. Suitable diluents include aromatic hydrocarbons such as toluene and primary alcohols such as isopropyl alcohol and butanol. Diluent may comprise 15 to 50% by weight of the nail lacquer composition.

Suspending agents are generally required to prevent settling of particulates, for example colour and pearl pigments, in lacquer compositions. Typical suspending agents for use in nail lacquer compositions are modified colloidal clays such as organically modified smectite, hectorite, bentonite, attapulgite or montmorillonite clays, for example stearalkonium hectorite. Such clays may be activated with dilute organic or inorganic acids such as phosphoric or citric acid to prepare thixotropic lacquers which are viscous enough to hold particulates in suspension but which are. sufficiently fluid after shaking or brushing to allow easy application. Suspending agent may comprise 0.05 to 5% by weight of the nail lacquer composition.

The compositions of the present invention may additionally comprise one or more further components which will be well known to those skilled in the art. These include colouring materials which are required to achieve the desired cosmetic effect such as colour, opacity, level and lustre of the film. Typical colour pigments include inorganic materials such as iron oxide, titanium dioxide and ferric ferrocyanide and organic lakes such as D & C Yellow No.5 Aluminium and D & C Red No.6 Barium lakes. Typical pearl pigments include titanium dioxide coated mica and bismuth oxychloride. Small amounts of solvent soluble organic dyes such as D & C Violet 2 may also be incorporated. Other typical nail lacquer components include, for example, ultraviolet absorbers such as drometrizole and benzophenones, gloss agents such as camphor and diacetone alcohol, talcs and fumed silicas (particularly in ridge fillers), matting agents such as microcrystalline waxes (particularly in base coats), agents which improve the properties of the nails themselves e.g. glyoxal and formaldehyde (particularly in nail hardeners), surfactants such as distearyl ammonium chloride, herbal extracts and perfumes.

In a particularly preferred embodiment the present invention provides a nail lacquer composition which comprises
a) 0.05 to 10% by weight of crystalline inorganic fibres having an aspect ratio of at least 2:1;
b) 8 to 30% by weight of nitrocellulose film former;
c) 2 to 20% by weight of resin;
d) 2 to 12% by weight of plasticiser;
e) 10 to 60% by weight of solvent; and
f) 0.05 to 5% by weight of suspending agent.

The handling and storage of nitrocellulose and the processing of colloidal clays are specialised operations. It is therefore commonplace in the industry to utilise standard nail lacquer base formulations commercially available from specialist suppliers. Typical base formulations are generally provided in the form of a suspension base comprising nitrocellulose film former, resin, solvent, diluent and colloidal clay suspending agent, and a corresponding reducing clear base composition from which suspending agent is omitted. To achieve the required nail lacquer composition a suitable suspension base is mixed with the desired combinations of, for example, colouring, pearlising and fibrous materials and the characteristics of the nail lacquer adjusted by addition of an appropriate amount of the reducing clear base composition. Typical nail varnish compositions contain about 85% by weight of suspension base and 5% by weight of reducing clear base. Typical base coats contain about 50% by weight of suspension base and 30 to 40% by weight of reducing clear base.

The characteristics of the nail lacquer compositions according to the invention may be evaluated, for example, as follows:

1. Viscosity and Rheology

Viscosity and theology were measured using a Brookfield Viscometer. Viscosity readings were taken on bulk compositions in a constant environment immediately after maximum shearing and after standing for 24 hours to obtain minimum and maximum (high and low shear) viscosity readings respectively. Rheology was determined from the viscosity recovery curve measured on bulk compositions in a constant environment after maximum shearing.

2. Hardness

A film 100 μm thick was applied with a hand coater (K-bar draw down equipment) to a smooth steel Q-panel. The hardness of the applied film was tested at various time intervals by marking with standard pencils of increasing hardness.

3. Adhesion

A film 100 μm thick was applied with a hand coater (K-bar draw down equipment) to a smooth steel Q-panel. The film was allowed to dry completely. A sharp fine-bladed knife was used to cut cross hatch lines in the film. Poor adhesion was demonstrated by film flaking in the squares. Further assessment of the degree of adhesion was determined by pressing adhesive tape onto the hatching and then stripping away.

4. Gloss

A film 50 μm thick was applied with a hand coater (K-bar draw down equipment) to a Morrest opacity chart. Readings of gloss were taken using a dual angle gloss meter.

5. Film strength and flexibility

Two films were applied to a silicone rubber sheet. The first film of 50 μm was applied with a hand coater (K-bar draw down equipment) and allowed to dry. A second film of 0.5 mm was then applied using a film forming channel (the first film allowed the film forming channel to move freely on the rubber sheet) and allowed to dry. The dry film was removed from the rubber sheet carefully and cut into dumbell shapes using a template and scalpel blade. The film was allowed to mature in a constant temperature environment before clamping into the jaws of a compression/tension measuring instrument (Instron). Load and extension of the film was recorded, from which film strength and flexibility was calculated.

The following Examples illustrate nail lacquer compositions according to the invention. These compositions have excellent characteristics of hardness, adhesion, film strength and flexibility whilst retaining satisfactory viscosity, theology and gloss characteristics.

EXAMPLE 1

| | | % w/w |
|---|---|---|
| 1) | Butyl acetate | 24–40 |
| 2) | Toluene | 16–30 |
| 3) | Ethyl acetate | 4–12 |
| 4) | Isopropyl alcohol | 2–6 |
| 5) | Butanol | 2–6 |
| 6) | Dibutyl phthalate | 4–12 |
| 7) | Acetone | 0.4–1.5 |
| 8) | Nitrocellulose resin | 8–20 |
| 9) | Polyester resin | 4–12 |
| 10) | Acrylic resin | 0.05–1 |
| 11) | UV Absorber | <0.1 |
| 12) | Camphor | 0.4–1.5 |
| 13) | Stearalkonium hectorite | 0.4–1.5 |
| 14) | Citric acid | 0.01–0.05 |
| 15) | Calcium sulphate hemihydrate fibre (sold under the trade name Franklin Fiber Filler H-30) | 0.14 |
| 16) | Pearl and Pigments | q.s. |
| | e.g. Bismuth oxychloride | 0.8 |
| | Titanium dioxide coated mica | 2.6 |
| | D & C Yellow No. 5 Al lake | 0.06 |

| | % w/w |
|---|---|
| D & C Red No. 6 Ba lake | 0.02 |
| Iron oxide | 0.005 |

Components 1 to 14 were formulated into a suspension base as follows. Nitrocellulose resin (component 8) was dissolved in butyl acetate (component 1). The secondary resins (components 9 and 10) and the camphor (component 12) were added and thoroughly mixed in. In a separate vessel citric acid activator (component 14) was added to stearalkonium hectorite master gel (10% in butyl acetate:toluene:ethyl acetate 3:2:1, commercially available from NL Chemicals, U.K.) and thoroughly mixed. The remaining solvents (components 3 to 7) were slowly added and mixed using a high shear mixer on slow speed to form a uniform pregel. The pregel was added to the resin/butyl acetate mixture and mixed thoroughly. Toluene diluent (component 2) was added and mixing at uniform speed continued until a homogeneous suspension base was obtained.

Components 1 to 12 were formulated into a reducing clear base as follows. Nitrocellulose resin (component 8) was dissolved in butyl acetate (component 1). The secondary resins (components 9 and 10) and the camphor (component 12) were added and thoroughly mixed in. The solvents (components 3 to 7) were mixed in followed by toluene diluent (component 2) and mixing was continued until a homogeneous reducing clear base was obtained.

The calcium sulphate fibres (component 15) were added to a mixture of the suspension base and the reducing clear base to give the nail varnish of Example 1. Pearl and pigments were optionally added to achieve the desired finished effect. Typically pigment was added as a colour paste produced from colour chips dispersed in suspension base, for example using grinding apparatus.

EXAMPLES 2 to 6

Different percentages of component 15 (Franklin Fiber) were formulated as described in Example 1 to give nail varnishes. The formulations of Examples 2, 3, 4, 5 and 6 contained 0.1, 0.5, 1.0, 2.5 and 5.0% by weight of component 15 respectively.

EXAMPLE 7

| | | % w/w |
|---|---|---|
| 1) | Butyl acetate | 8–25 |
| 2) | Toluene | 20–50 |
| 3) | Ethyl acetate | 4–10 |
| 4) | Isopropyl alcohol | 8–25 |
| 5) | Dibutyl phthalate | 4–10 |
| 6) | Nitrocellulose resin | 8–25 |
| 7) | Toluene sulphonamide-formaldehyde resin | 4–10 |
| 8) | UV Absorber | <0.1 |
| 9) | Camphor | 0.5–5 |
| 10) | Stearalkonium hectorite | 0.5–5 |
| 11) | Citric acid | 0.01–0.05 |
| 12) | Calcium metasilicate fibre (sold under the trade name Kemolit Wollastonite S4) | 0.14 |
| 13) | Pearl and Pigments | q.s. |

Components 1 to 11 and 1 to 9 were formulated as described in Example 1 to prepare a suspension base and a reducing clear base respectively. Components 13 were evenly dispersed into a small portion of the suspension base using grinding apparatus and then mixed, together with component 12, into a mixture of the suspension base and the reducing clear base (using a low shear mixer) to give the nail varnish of Example 7.

EXAMPLES 8 to 12

Different percentages of component 12 (Kemolit Wollastonite S4) were formulated as described in Example 7 to give nail varnishes. The formulations of Examples 8, 9, 10, 11 and 12 contained 0.1, 0.5, 1.0, 2.5 and 5.0% by weight of component 12 respectively.

EXAMPLE 13

| | | % w/w |
|---|---|---|
| 1) | Methyl methacrylate | 3.0 |
| 2) | Methyl/Butyl methacrylate | 8.0 |
| 3) | Ethyl methacrylate | 20.0 |
| 4) | Butyl acetate | 25.0 |
| 5) | Ethyl acetate | 16.0 |
| 6) | Isopropyl alcohol | 3.0 |
| 7) | Toluene | 24.8 |
| 8) | Calcium sulphate hemihydrate (sold under the trade name Franklin Fiber Filler H-30) | 0.2 |

Components 1 to 3 were dissolved in a mixture of components 4 to 7. Component 8 was mixed into the bulk composition using a low shear mixer to give the top coat formulation of Example 13.

EXAMPLE 14

| | | % w/w |
|---|---|---|
| 1) | Butyl acetate | 24–40 |
| 2) | Toluene | 16–30 |
| 3) | Ethyl acetate | 4–12 |
| 4) | Isopropyl alcohol | 2–6 |
| 5) | Butanol | 2–6 |
| 6) | Dibutyl phthalate | 4–12 |
| 7) | Acetone | 0.4–1.5 |
| 8) | Nitrocellulose resin | 8–20 |
| 9) | Polyester resin | 4–12 |
| 10) | Acrylic resin | 0.05–1 |
| 11) | UV Absorber | 0.1 |
| 12) | Camphor | 0.4–1.5 |
| 13) | Stearalkonium hectorite | 0.2–1.5 |
| 14) | Citric acid | 0.01–0.05 |
| 15) | Microcrystalline wax | 4.5 |
| 16) | Calcium sulphate hemihydrate fibre (sold under the trade name Franklin Fiber Filler H-30) | 5.0 |
| 17) | Colour | q.s. |

Components 1 to 14 and 1 to 12 were formulated as described in Example 1 to prepare a suspension base and a reducing clear base respectively. Components 15 and 17 were evenly dispersed into a small portion of the suspension base using grinding apparatus and then mixed, together with component 16, into a mixture of the suspension base and the reducing clear base (using a low shear mixer) to give the base coat formulation of Example 14.

EXAMPLES 15 and 16

Different percentages of component 16 (Franklin Fiber) were formulated as described in Example 14 to give base coats. The formulations of Examples 15 and 16 contained 1.0 and 2.5 % by weight of component 16 respectively.

EXAMPLE 17

|  |  | % w/w |
|---|---|---|
| 1) | Methyl methacrylate | 3.0 |
| 2) | Methyl/Butyl methacrylate | 8.0 |
| 3) | Ethyl methacrylate | 20.0 |
| 4) | Butyl acetate | 24.0 |
| 5) | Ethyl acetate | 16.0 |
| 6) | Isopropyl alcohol | 3.0 |
| 7) | Toluene | 23.4 |
| 8) | Calcium sulphate hemihydrate fibre (sold uner the trade name Franklin Fiber Filler H-30) | 0.2 |
| 9) | Attapulgite clay | 2.0 |
| 10) | Distearyl ammonium chloride | 0.4 |
| 11) | Colour | q.s. |
|  | e.g. D & C Violet No. 2 | <0.01 |

Surfactant (component 10) was dispersed into the butyl acetate (component 4) and the clay (component 9) gradually dispersed therein using a high shear mixer to form a pregel. Components I to 1 3 were dissolved in a mixture of components 5 to 7 and the pregel mixed into the bulk composition using a low shear mixer. Components 11 were evenly dispersed into a small portion of the base composition using grinding apparatus. Alternatively, commercially available colour chips in acrylic resin can be used after dispersion into the required solvent using a disintegrater e.g. Torrance mixer. The pigment dispersion was mixed into the bulk composition, together with component 8, using a low shear mixer to give the nail varnish of Example 17.

I claim:

1. A nail lacquer composition which comprises film former, solvent and 0.05 to 10% by weight of crystalline calcium sulphate fibers having an aspect ratio of at least 2:1.

2. A nail lacquer composition according to claim 1 which comprises
   a) 0.05 to 10% by weight of calcium sulphate fibres having an aspect ratio of at least 2:1;
   b) 8 to 30% by weight of nitrocellulose film former;
   c) 2 to 20% by weight of resin;
   d) 2 to 12% by weight of plasticiser;
   e) 10 to 60% by weight of solvent; and
   f) 0.05 to 5% by weight of suspending agent.

3. A nail lacquer composition according to claim 1 which comprises 0.05 to 5% by weight of fibres having an aspect ratio of at least 2:1.

4. A nail lacquer composition according to claim 1 which comprises 0.05 to 5% by weight of fibres having an aspect ratio of at least 4:1.

5. A nail lacquer composition according to claim 1 in which the calcium sulphate fibre is a single crystal whisker fibre.

6. A nail lacquer composition according to claim 1 which comprises 0.1 to 1% by weight of fibres.

7. A nail lacquer composition according to claim 2 which comprises 0.05 to 5% by weight of fibers having an aspect ratio of at least 4:1.

8. A nail lacquer composition according to claim 7 which comprises 0.1 to 1% by weight of fibers.

9. A nail lacquer composition according to claim 8 in which the calcium sulphate fibre is a single crystal whisker fibre.

10. A nail lacquer composition according to claim 1 which further comprises 15 to 50% by weight of a diluent miscible with the film former.

11. A nail lacquer composition which comprises
    a) 0.05 to 10% by weight of calcium sulphate fibers having an aspect ratio of at least 2:1;
    b) at least one film former selected from the group consisting of 8 to 30% by weight of nitrocellulose and 12 to 55% by weight of acrylic acid ester;
    c) 10 to 60% by weight of solvent selected from the group consisting of acetone, diacetone alcohol, ethyl acetate, butyl acetate, toluene and isopropyl alcohol;
    d) 0.05 to 5% by weight of colloidal clay suspending agent;
    e) 2 to 20% by weight of resin selected from the group consisting of aryl sulphonamideformaldehyde, acrylic and polyester resins; and
    f) 2 to 12% by weight of plasticizer selected from the group consisting of castor oil and dibutyl phthalate.

12. A nail lacquer composition according to claim 11 in which the acrylic acid ester is selected from the group consisting of methyl, ethyl and butyl methacrylate.

13. A nail lacquer composition according to claim 11 in which the colloidal clay suspending agent is selected from the group consisting of smectite, hectorite, bentonite, attapullgite and montmorillonite.

14. A nail lacquer composition according to claim 11 containing 0.05 to 5% by weight of fibers.

15. A nail lacquer composition according to claim 14 in which the fibers have an aspect ratio of at least 4:1.

16. A nail lacquer composition according to claim 15 in which the amount of fibers is 0.1 to 1% by weight.

17. A nail lacquer composition according to claim 11 further containing 15 to 50% of a diluent miscible with the film former.

18. A nail lacquer composition according to claim 11 in which the calcium sulphate fibre is a single crystalline whisker fibre.

* * * * *